United States Patent [19]

Temsamani et al.

[11] Patent Number: 5,693,466
[45] Date of Patent: Dec. 2, 1997

[54] DETECTION OF SYNTHETIC OLIGONUCLEOTIDES EXTRACTED FROM BODY FLUIDS OR TISSUES

[75] Inventors: Jamal Temsamani; Sudhir Agrawal, both of Shrewsbury, Mass.

[73] Assignee: Hybridon, Inc., Worcester, Mass.

[21] Appl. No.: 368,243

[22] Filed: Jan. 3, 1995

Related U.S. Application Data

[63] Continuation of Ser. No. 56,363, Apr. 30, 1993, abandoned, Continuation-in-part of Ser. No. 2,786, Jan. 8, 1993, abandoned.

[51] Int. Cl.$^6$ .................................................. C12Q 1/68
[52] U.S. Cl. ..................................... 435/6; 336/24.3
[58] Field of Search ............................ 435/6; 536/24.3

[56] References Cited

U.S. PATENT DOCUMENTS

| | | | |
|---|---|---|---|
| 4,483,920 | 11/1984 | Gillespie et al. | 435/6 |
| 5,118,605 | 6/1992 | Urdea | 435/6 |
| 5,149,798 | 9/1992 | Agrawal et al. | 536/27 |
| 5,223,402 | 6/1993 | Abbas et al. | 435/18 |

FOREIGN PATENT DOCUMENTS

| | | |
|---|---|---|
| WO88 08036 | 10/1988 | European Pat. Off. . |
| 0324474A1 | 7/1989 | European Pat. Off. . |
| WO92 00983 | 1/1992 | European Pat. Off. . |
| WO92 18649 | 10/1992 | European Pat. Off. . |

OTHER PUBLICATIONS

U.S. Patent application 08/002,786, Temsamani et al.
Seibl et al. Non–radioactive Labeling and Detection of Nucleic Acids III. Applications of the Digoxigenin System, Biol. Chem. Hoppe–Seyler (Oct. 1990) 371:939–951.
Agrawal et al. in *Gene Regulation: Biology of Antisense RNA and DNA* (Erikson and Izant, eds.) Raven Press Ltd., New York (1992) pp. 273–283).
Agrawal (1992) *Trends in Biotechnology* 10:152–158.
Matsukura et al. in *Prospects for Antisense Nucleic Acid Therapy of Cancer and AIDS*, Wiley–Lisss, Inc. (1992) pp. 159–178.
Agrawal (1991) in *Prospects for Antisense Nucleic Acid Therapy of Cancer and AIDS*, (Wickstrom, ed.) Liss, New York, pp. 143–158.
Agrawal et al. (1991) *Proc. Natl. Acad. Sci* (USA) 88:7595–7599.
Vickers et al. (1991) *Nucleic Acids. Res.* 19:3359–3368.
Agrawal et al. (1989) *Proc. Natl. Acad. Sci.* (USA) 86:7790–7794.
Matsukura et al. (1989) *Proc. Natl. Acad. Sci.* (USA) 86:4244–4248.
Agrawal et al. (1988) *Proc. Natl. Acad. Sci.* (USA) 85:7–7079–7083.
Goodchild et al. (1988) *Proc. Natl. Acad. Sci.* (USA) 85:5507–5511.
Matsukura et al. (1988) *Gene* 72:343–347.
Sarin et al. (1988) *Proc. Natl. Acad. Sci.* (USA) 85:7448–7451.
Wickstrom (1986) *J. Biochem. Biophys. Meth.* 13:97–102.
Zamecnik et al. (1986) *Proc. Natl. Acad. Sci.* (USA) 83:4143–4147.
Southern (1975) *J. Mol. Biol.* 98:503–517.

*Primary Examiner*—Kenneth R. Horlick
*Assistant Examiner*—Joyce Tung
*Attorney, Agent, or Firm*—McDonnell Boehnen Hulbert & Berghoff

[57] ABSTRACT

The invention provides a method for detecting specific synthetic oligonucleotides that are present in body fluid or tissue samples taken from an animal or human patient to whom oligonucleotides have been administered.

12 Claims, 3 Drawing Sheets

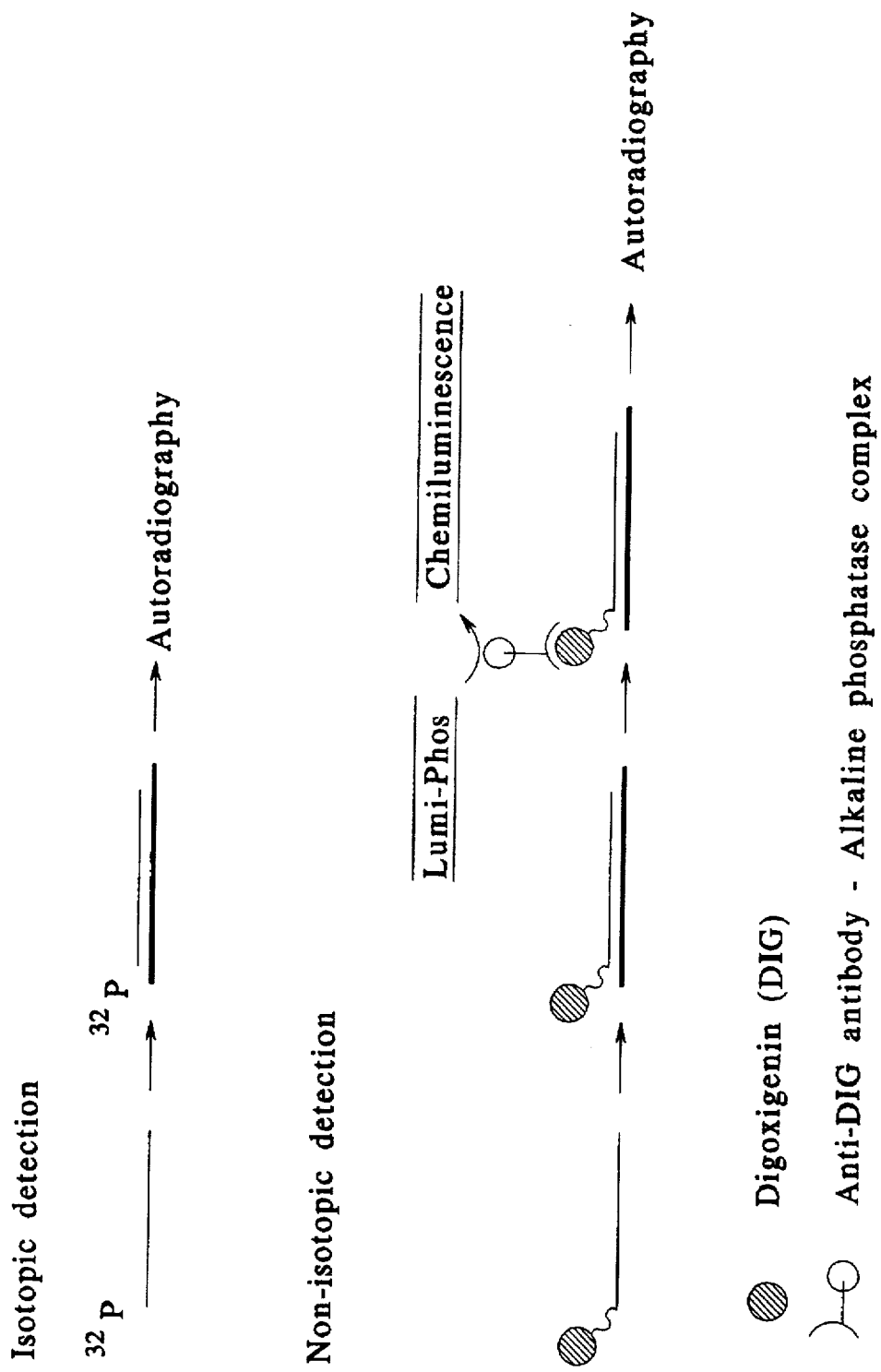

DETECTION OF SYNTHETIC OLIGONUCLEOTIDES EXTRACTED FROM BODY FLUIDS OR TISSUES

This application is a continuation of application Ser. No. 08/056,363, filed Apr. 30, 1993, abandoned, which is a continuation-in-part of application Ser. No. 08/002,786 filed Jan. 8, 1993, now abandoned.

BACKGROUND OF THE INVENTION

1. Field of the Invention

The invention relates to the detection of specific nucleic acid sequences. More particularly, the invention relates to the detection of synthetic oligonucleotides present in body fluids or tissues.

2. Summary of the Related Art

Detection of specific nucleic acid sequences present in cells is generally known in the art. Southern, J. Mol. Biol. 98:503-517 (1975) teaches detection of specific sequences among DNA fragments separated by gel electrophoresis, using "blotting" or transfer of the DNA fragments to a membrane, followed by hybridization of denatured DNA fragments with a radioactive probe and autoradiography. This procedure has also been extended to the detection of RNA molecules extracted from cells or tissues. More recently, faster and quantitative "dot-blotting" procedures have been developed for rapid detection of DNA or RNA from tissues or cells.

Recently, considerable interest has been generated in the development of synthetic oligonucleotides as therapeutic or gene expression modulating agents in the so-called antisense approach. For example, Agrawal, Trends in Biotechnology 10:152-158 (1991) extensively reviews the development of antisense therapeutic approaches. For an antisense therapeutic approach to be effective, oligonucleotides must be introduced into a patient and must reach the specific tissues to be treated. Consequently, there is a need to be able to detect oligonucleotides in body fluids or tissues. In animal models, radiolabelled oligonucleotides have been administered to the animal and their distribution within body fluids and tissues has been assessed by extraction of the oligonucleotides followed by autoradiography (See Agrawal, Temsamani and Tang, Proc. Natl. Acad. Sci. 88:7595-7599 (1991). As a practical matter, however, these methods cannot be extended to human patients. Unfortunately, the various techniques for detecting specific unlabelled nucleic acid sequences present in body fluids or tissues has only been extended to polynucleotides, such as large DNA or RNA molecules. Due to the small size of oligonucleotides, special problems relating to nonspecific binding or background, as well as to absence of binding, nondetection or false negatives exist. Thus, there remains a need to develop procedures for the detection of specific synthetic oligonucleotide sequences present in body fluids and tissues.

BRIEF SUMMARY OF THE INVENTION

The invention provides a method for detecting the presence of synthetic oligonucleotides in body fluids or tissue samples taken from a laboratory animal or a human patient. In the method according to the invention, body fluid or tissue samples are taken from an animal or human to whom an oligonucleotide has been administered and are proteolytically digested, then extracted. Total nucleic acids are then transferred to a hybridization membrane. The hybridization membrane with attached nucleic acids is prehybridized, then hybridized with a labelled oligonucleotide that is complementary to the oligonucleotide that was administered to the animal or patient. Presence of hybridized, labelled oligonucleotide is then detected by standard procedures. The method according to the invention is useful both for detection and localization of oligonucleotides in patients undergoing antisense oligonucleotide therapy and in animal models used in studies for pharmacokinetic properties of oligonucleotides.

BRIEF DESCRIPTION OF THE DRAWINGS

FIGS. 1A and 1B show the autoradiography and densitometry. FIG. 1C shows a plot of the scanning densitometry of the autoradiograph versus known concentration of oligonucleotide.

FIG. 2 illustrates applications of the method according to the invention using either isotopic or non-isotopic detection.

DETAILED DESCRIPTION OF THE PREFERRED EMBODIMENTS

Figure 1A:
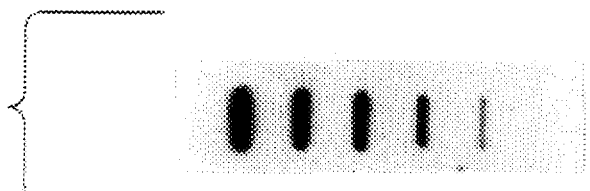
FIGS. 1A-1C show autoradiography results obtained from the experiments described in Examples 1-5 using radiolabeled probe.
Figure 1B:
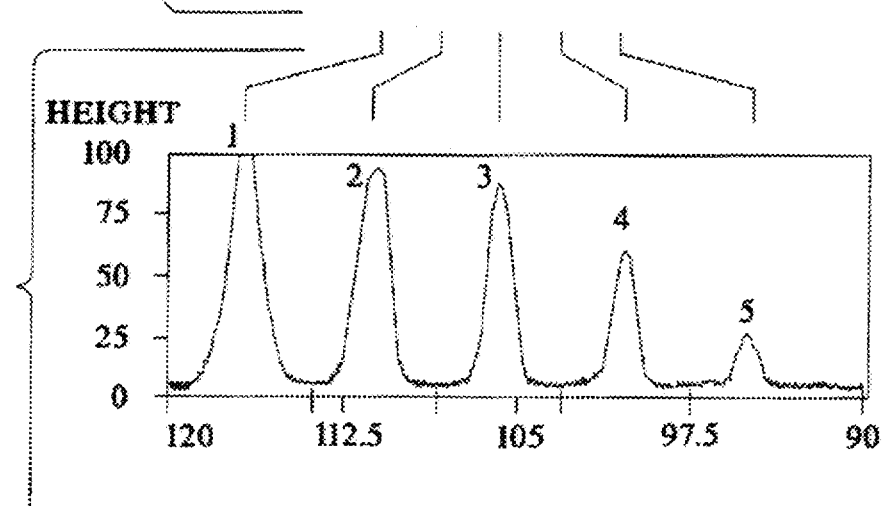

The invention relates to the detection of specific nucleic acid sequences present in body fluids or tissues. In particular, the invention relates to the detection of synthetic oligonucleotides in body fluids or tissues of an animal or human patient to whom such oligonucleotides have been administered.

The invention provides a method of detecting synthetic oligonucleotides extracted from body fluids or tissues. As used herein, "oligonucleotides" include, but are not limited to, all polymers of 5' to 3' linked ribonucleosides, 2'-modified ribonucleosides and/or deoxyribonucleosides wherein the linkage may be a natural phosphodiester linkage or an artificial linkage, such as a phosphorothioate, phosphorodithioate, phosphoramidate, alkylphosphonate, akylphosphonothioate, sulfonate, carbamate or phosphotriester linkage. Moreover, such oligonucleotides encompass oligonucleotides having modifications on the bases and/or sugar residues as well as those having nuclease resistance-conferring bulky substituents at the 3' and/or 5' end. As used herein, "body fluids" include, but are not limited to, blood, urine, sweat, mucous secretions, cerebrospinal fluid and synovial fluid. When blood is used, it is preferred to spin out the cells to obtain serum or plasma and to extract the nucleic acids from the serum or plasma. "Tissues" include those constituting any organ, such as lymphoid tissue, liver, kidney, lung, brain, intestine, smooth muscle, cardiac muscle, striated muscle, dermis and epidermis, among others.

In the method according to the invention, a sample of body fluid or a tissue sample is treated in the following manner. First, the body fluid is proteolytically digested with an appropriate protease, such as proteinase K, pronase, or another conventional protease. Next, the sample is extracted with a partitioning agent, preferably with phenol/chloroform/isoamyl alcohol. Then, nucleic acids are extracted with isobutanol and ethyl ether. Next, the nucleic acids are resuspended into solution, rendered single stranded and applied and bonded to an appropriate hybridization membrane. Such membranes include, but are not limited to, nylon and Pall A membranes. Next, the membrane having bound nucleic acids is treated with a labelled oligonucleotide that is complementary to the oligonucleotide to be detected. The Complementary oligonucleotide is allowed to hybridize, then unhybridized oligonucleotide is washed away. Appropriate labels include radioisotope labels, such as $^{32}$P or $^{35}$S, as well as any other conventional label, such as a fluorescent label like rhodamine or fluorescein, a chemoluminescent label, or biotin and enzymes.

Such labels may be incorporated directly onto the oligonucleotide probe. Alternatively, in a preferred embodiment, an antigen is attached to the oligonucleotide and the label is attached to the probe (which is hybridized to its target sequence) by coupling the label to an antibody that specifically binds to the antigen. A most preferred embodiment utilizes a probe to which the antigen digoxygenin (DIG) is bound, and an anti-DIG antibody or antigen-binding antibody fragment that is conjugated to alkaline phosphatase. In this embodiment, the probe is detected by adding a stable phosphorylated compound which, upon dephosphorylation, emits luminescence that is detectable by autoradiography. For purposes of the invention, the term "autoradiography" is intended to encompass exposure of photographic film by juxtaposition of the film with a probe-hybridized hybridization membrane, regardless of whether the exposure is effected by light, by x-ray, or by alpha or beta particles or gamma rays emitted upon decay of a radioactive compound. Those skilled in the art will recognize that any other antigen can be used in place of DIG and will be functionally equivalent to DIG in the method according to the invention. Those skilled in the art will also recognize that other ligand-receptor pairs can be substituted for the antigen antibody pair and will be functional equivalents thereof. Finally, those skilled in the art will recognize that any other enzyme-substrate combination that produces chemiluminescence can be substituted for the alkaline phosphatase and its reagent and will be functional equivalent thereof.

Hybridization and wash conditions are especially important. For oligonucleotides having ionic internucleotide linkages, such as oligonucleotide phosphodiesters or phosphorothioates, in 6x SSC, 3–16 hours of hybridization at 37° C., followed by two five to ten minute washes in 6x SSC at room temperature was found to be appropriate for detection of a 25-mer oligonucleotide with 56% G+C content, using a 25-mer probe having 62% G+C content. At higher stringencies, target oligonucleotide is not detected, whereas at lower stringencies background hybridization obscures true signal. For oligonucleotides having nonionic modified internucleotide linkages or lower G+C content, lower stringency (e.g., lower temperatures, higher salt concentrations) may be helpful. For longer oligonucleotides or for oligonucleotides having higher G+T content or RNA components, increases in stringency (e.g., higher temperatures, lower salt concentrations, and/or presence of hydrogen bond competitors such as formamide) may be useful. The relationship between melting temperatures and various modified internucleotide linkages has been well described (see e.g., FIG. 9 of U.S. Pat. No. 5,149,798, the teachings of which are hereby incorporated by reference). For any given modified oligonucleotide, hybridization conditions should first be worked out by starting at the conditions described in Example 4, below, using a target oligonucleotide blotted directly to the hybridization membrane. Then, stringency can be reduced or increased to account for the modifications until a limit of detection of about 3 ng target oligonucleotide is reached. It is at this level that the problems of both background and nondetection were eliminated.

Following washing, the membrane is dried and the signal is detected by conventional means, such as fluorescence detection, β-emission detection, chemiluminescence detection, or autoradiography.

The method according to the invention is useful in animal studies of oligonucleotide pharmacokinetics, and eliminates the need to use large quantities of radiolabelled oligonucleotides in the animal. In addition, the method according to the invention is useful for detecting oligonucleotide concentration and distribution in a human patient undergoing antisense oligonucleotide therapy, thereby facilitating dosage optimization.

The following examples are intended to further illustrate certain preferred embodiments of the invention and are not limiting in nature.

EXAMPLE 1

Preparation of Body Fluid and Tissue Samples

Serum or blood was spiked with known quantities of oligonucleotide. 250 μl of spiked blood serum was incubated in 250 μl extraction buffer (0.5% SDS/10 mM NaCl/20 mM Tris-HCl, pH 7.6/10 mM EDTA) containing 2 mg/ml proteinase K for 1.5 to 2 hours at 60° C. Two hundred microliters of water were added to the samples, which were then extracted once with 500 μl phenol/chloroform/isoamyl alcohol (25:24:1 vol/vol) and once with 500 μl chloroform. The aqueous phase was then extracted twice with 1 ml isobutanol and once with 500 μl ethyl ether. The remaining solution, containing nucleic acids was dried to a pellet. Pellets were resuspended in 10 ul TE buffer (10 mM Tris-HCl, pH 8.0/1 mM EDTA) then heated to 95° C. for 5 minutes. Forty ul 20x SSC (3M NaCl/0.3M sodium citrate, pH 7.0) was then added. Similar treatment can be carried out using as little as 500 μl urine or 0.25 cm$^3$ lymphoid tissue.

EXAMPLE 2

Transfer of Extracted Nucleic Acids to a Membrane

One piece each of Nylon membrane (Zeta Probe™, BiO Rad)) and Whatman 3MM paper were wetted in 10 x SSC. Wetted Whatman paper was placed in a dot blot apparatus (Minifold II™, Schleicher & Schuell) and the wetted nylon membrane was placed atop the Whatman paper. The multiple-well lid was placed on the apparatus and latched in place, then the apparatus was hooked up to a vacuum source. Wells were rinsed with 100 μl 20 x SSC, then samples prepared according to Example 1 were added in 10 μl TE+40 ml 20X SSG to the wells. Wells were then rinsed with 100 μl 20 x SSC. Vacuum was then turned off and the nylon membrane removed. The nylon membrane was then exposed for 10 minutes to short wave (<300 nm) UV light at a distance of 10 cm with the topside of the membrane facing the UV source to cross-link nucleic acids to the membrane.

EXAMPLE 3

Preparation of Labelled Probe

For preparation of radiolabelled probe, an oligonucleotide complementary to the oligonucleotide used to spike the blood, urine or tissue samples was labelled with $^{32}$P at its 5' end in a reaction mixture containing 100 ng oligonucleotide (5 μl), 3 μl [gamma—$^{32}$P] ATP (3,000 Ci/mmole at 10mCi/ml), 1 μl 10x kinase buffer and 1 μl T4 polynucleotide kinase (8–10 units/μl) at 37° C. for 30 minutes, then heated to 65° C. for 3 minutes. Labelled oligonucleotide was then precipitated with 0.4M NH$_4$OAc and ethanol and resuspended in 50 μl of H$_2$O.

Alternatively, nonradioactive chemiluminescent probes were prepared using the Genius 5™ Oligonucleotide Tailing Kit (Boehringer Mannheim) according to the manufacturer's instructions. One μg oligonucleotide was 3' tailed with Digoxygenin-11-dduTP/dATP (DIG-11-dduTP/dATP) in the presence of terminal transferase. The 20 μl reaction mixture volume contained 4 μl 5x reaction buffer (1M potassium cacodylate, 125 mM Tris.HCl, 1.25 mg/ml bovine serum albumin, pH 6.6 at 25° C.), 4 μl 25 mM cobalt chloride, 100 picomoles oligonucleotide, 1 μl 1 mM DIG-11-dduTP (2', 3'dideoxyuridine-5'-triphosphate coupled to digoxygenin via an 11 atom spacer arm), and 50 units terminal transferase. The reaction mixture was incubated at 37° C. for 15 minutes, then placed on ice. One μl 20 mg/ml glycogen and 1 μl 200 mM EDTA (pH8.0) were added to the reaction mixture, which was then precipitated by adding 0.1 volume 4M lithium chloride and 2.5 volumes of chilled ethanol, then mixing and incubating at −70° C. for 30 minutes. The oligonucleotide was pelleted and the pellet was washed with 70% ethanol, direct and resuspended in 30 μl 10 mM Tris-HCl (pH7.0–8.0)/1 mM EDTA/1% SDS.

EXAMPLE 4

Prehybridization and Hybridization of Probe Oligonucleotide

The membrane prepared according to Example 2 was prehybridized in 10 ml hybridization buffer (1M NaCl/1% SDS/10% dextran sulfate and 150 μg/ml tRNA) for 1 to 3 hours at 37° C. To the membrane in hybridization solution was added labelled oligonucleotide probe diluted with 3 μg/ml final concentration unlabelled complementary oligonucleotide ($5 \times 10^5$ cpm/ml; 250 ng/ml probe final concentration) and incubation was continued for 3–16 hours at 37° C. The membrane was washed twice (5–10 minutes per wash) in 6x SSC, then dried at room temperature.

EXAMPLE 5

Detection of Probe Specifically Bound to Membrane

Detection of probe specifically bound to the membrane, as prepared according to Example 4, was carried out as follows. The membrane was exposed to X-ray film, which was then developed and subjected to scanning densitometry, with comparison to samples of known quantities of oligonucleotide that had been directly blotted to the membrane. The results demonstrate detection of about 3 ng oligonucleotide per 0.25 ml serum. Similar results are obtained for urine and tissue samples.

Figure 1C:
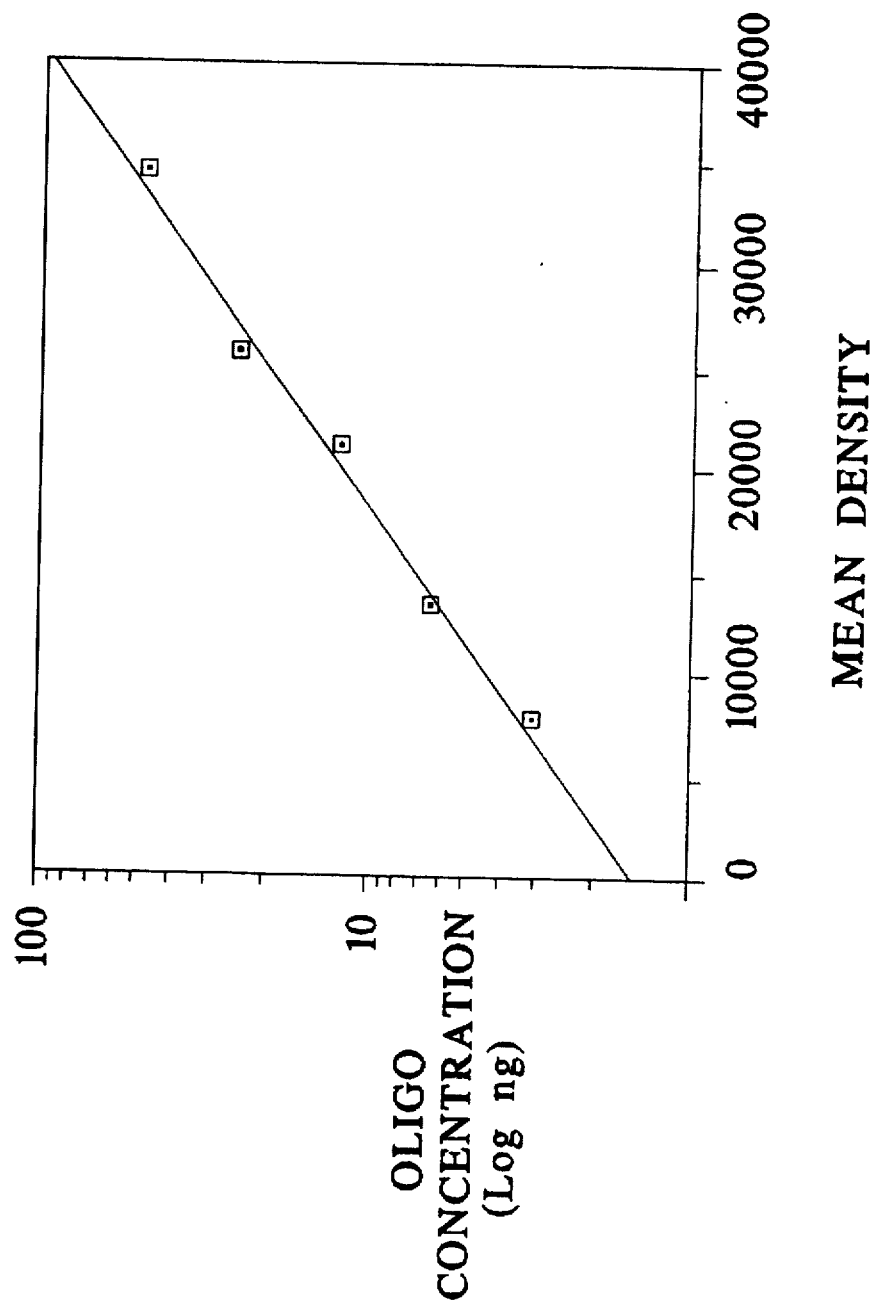

In experiments in which the antigen DIG was attached to the probe, probe was detected by the binding of alkaline phosphatase-conjugated anti-DIG antibody Fab fragment, using the Genius 3™ Nucleic Acid Detection Kit (Boehringer Mannheim) according to the manufacturer's directions. Briefly, the hybridization membrane having specifically bound probe oligonucleotide, prepared as described in Example 4, was blocked for 30–60 minutes with a blocking agent in a solution of 100 mM Tris-HCl (pH7.5)/150 mM NaCl, then an anti-DIG antibody Fab fragment conjugated to alkaline phosphatase, in the same solution, was added to the membrane. The antibody solution was incubated with the membrane for 30 minutes, then the membrane was removed and placed in a new hybridization bag. The membrane was then washed twice at room temperature, 15 minutes per wash, in 100 mM Tris-HCl (pH 7.5)/150 mM NaCl, which was previously filtered through a 0.45 μM filtration membrane. After the washes, with the membrane still wet, the membrane was placed between 2 sheets of acetate. Then, 0.5 ml (per 100 cm² membrane) of 0.33 mM 4-methoxy-4-(3-phosphatephenyl)-spiro(1, 2'dioxetane-3,2'-adamantane) disodium salt/750 mM 2-amino-2-methyl-1propanol (pH 9.6)/0.88 mM $MgCl_2$/1.13 mM cetyltrimethylammonium bromide/0.035 mM fluorescein surfactant was applied to the top surface of the membrane and a liquid seal was allowed to form between the membrane and the acetate sheets. The acetate covered membrane was then used to expose a sheet of XAR™ film (Kodak) for 60 minutes. The exposed film was developed then scanned into a computer using a densitometer and RV 934 version 2.0 densitometry software (EC Apparatus Corporation). The mean densities were then plotted against the known concentrations of the oligonucleotide. The results are shown in FIG. 1C.

These results demonstrate that the method according to the invention can detect oligonucleotides present at a concentration as low as 3 ng/ml in body fluids or tissues. In addition, the method according to the invention can be used to quantitate oligonucleotides present in body fluids or tissues.

We claim:

1. A method of detecting synthetic oligonucleotides that are present in body fluids or tissues, said oligonucleotides being extractable with isobutanol and ethyl ether, the method comprising the steps of:
    (a) proteolytically digesting a body fluid or tissue sample;
    (b) extracting the proteolytically digested sample with a partitioning agent;
    (c) extracting the aqueous phase in the extracted sample with isobutanol and ethyl ether,
    (d) drying the remaining solution containing nucleic acids to a pellet and resuspending the nucleic acids into a solution;
    (e) binding the nucleic acids to a hybridization membrane;
    (f) treating the membrane having bound nucleic acids with a labeled oligonucleotide probe that is complementary to and specifically binds to the synthetic oligonucleotide to be detected;
    (g) washing the membrane to remove any labeled oligonucleotide that is not specifically hybridized to nucleic acids bound to the membrane; and
    (h) detecting the presence of the probe on the membrane.

2. The method according to claim 1, wherein the body fluid is blood.

3. The method according to claim 1, wherein the body fluid is urine.

4. The method according to claim 1, wherein the tissue is lymphatic tissue.

5. The method according to claim 1, wherein the labelled oligonucleotide probe is a radiolabeled probe.

6. The method according to claim 1, wherein the labeled oligonucleotide probe comprises an oligonucleotide labeled with an antigen to which an antigen-binding antibody or antibody fragment can bind or with a ligand to which a ligand-binding receptor can bind, and wherein the detection of the probe comprises the steps of:
    (a) blocking the membrane with a suitable blocking agent to prevent non-specific attachment to the membrane of the antigen-binding antibody or antibody fragment or ligand-binding receptor;
    (b) incubating the membrane with an antigen-binding antibody, antibody fragment or receptor that specifically binds to the antigen or ligand and is conjugated to an enzyme that acts upon a substrate to produce chemiluminescence;

(c) washing the membrane to remove any non-specifically bound antibody, antigen-binding antibody fragment or receptor;

(d) adding the substrate upon which the enzyme acts; and (e) exposing the membrane to photographic film.

7. A method of detecting the presence in body fluids or tissues of a synthetic oligonucleotide, the method comprising detecting the presence on a membrane of an oligonucleotide duplex formed by a labeled oligonucleotide probe hybridized to the synthetic oligonucleotide to be detected, said synthetic oligonucleotide capable of being extracted by isobutanol and ethyl ether, the oligonucleotide duplex on the membrane having been prepared by:

(a) proteolytically digesting a body fluid or tissue sample;

(b) extracting the proteolytically digested sample with a partitioning agent;

(c) extracting the aqueous phase in the extracted sample with isobutanol and ethyl ether;

(d) drying the remaining solution containing nucleic acids to a pellet and resuspending the nucleic acids into a solution;

(e) binding the nucleic acids to a hybridization membrane;

(f) treating the membrane having bound nucleic acids with a labeled oligonucleotide probe that is complementary to and specifically binds to the synthetic oligonucleotide to be detected;

(g) washing the membrane to remove any labeled oligonucleotide that is not specifically hybridized to nucleic acids bound to the membrane.

8. The method according to claim 7, wherein the body fluid is blood.

9. The method according to claim 7, wherein the body fluid is urine.

10. The method according to claim 7, wherein the tissue is lymphatic tissue.

11. The method according to claim 7, wherein the labeled oligonucleotide probe is a radiolabeled probe.

12. A method according to claim 7, wherein the labeled oligonucleotide probe comprises an oligonucleotide labeled with an antigen to which an antigen-binding antibody or antibody fragment can bind or with a ligand to which a ligand-binding receptor can bind, and wherein the detection of the oligonucleotide duplex further comprises exposing to photographic film the membrane of claim 7 that has further been prepared by:

(a) blocking the membrane having with a suitable blocking agent to prevent non-specific attachment to the membrane of the antigen-binding antibody or antibody fragment or ligand-binding receptor;

(b) incubating the membrane with an antigen-binding antibody, antibody fragment or receptor that specifically binds to the antigen or ligand and is conjugated to an enzyme that acts upon a substrate to produce chemiluminescence;

(c) washing the membrane to remove any non-specifically bound antibody, antigen-binding antibody fragment or receptor;

(d) adding the substrate upon which the enzyme acts.

* * * * *